US008245712B2

(12) United States Patent
Kling

(10) Patent No.: US 8,245,712 B2
(45) **Date of Patent: *Aug. 21, 2012**

(54) RESPIRATOR MASK FOR A COMPRESSED AIR BREATHING APPARATUS

(75) Inventor: Peter Kling, Berlin (DE)

(73) Assignee: MSA Auer GmbH, Berlin (DE)

( * ) Notice: Subject to any disclaimer, the term of this patent is extended or adjusted under 35 U.S.C. 154(b) by 200 days.

This patent is subject to a terminal disclaimer.

(21) Appl. No.: 12/687,522

(22) Filed: Jan. 14, 2010

(65) Prior Publication Data

US 2011/0226251 A1 Sep. 22, 2011

Related U.S. Application Data

(63) Continuation of application No. 10/497,134, filed as application No. PCT/DE02/03420 on Sep. 10, 2002, now Pat. No. 7,673,630.

(30) Foreign Application Priority Data

Nov. 27, 2001 (DE) ................................. 101 59 219

(51) Int. Cl.

| | |
|---|---|
| ***A62B 18/10*** | (2006.01) |
| ***A62B 18/02*** | (2006.01) |
| ***A62B 18/08*** | (2006.01) |
| ***A62B 9/02*** | (2006.01) |
| ***A62B 9/04*** | (2006.01) |
| ***A62B 18/00*** | (2006.01) |
| ***A61M 16/00*** | (2006.01) |

(52) U.S. Cl. ......... 128/207.12; 128/206.28; 128/206.21; 128/206.15; 128/206.12; 128/205.25; 128/205.24; 128/202.27; 128/201.22; 128/201.24; 128/201.23; 128/205.15

(58) Field of Classification Search ............. 128/207.12, 128/206.28, 206.21, 206.15, 206.12, 205.25, 128/205.24, 202.27, 201.22, 201.24, 201.23, 128/205.15

See application file for complete search history.

(56) References Cited

U.S. PATENT DOCUMENTS

| | | | | |
|---|---|---|---|---|
| 3,957,044 | A | 5/1976 | Fletcher et al. | |
| 4,306,584 | A | 12/1981 | Schlobohm | |
| 4,856,120 | A | 8/1989 | Hart | |
| 4,961,420 | A | 10/1990 | Cappa et al. | |
| 5,499,624 | A * | 3/1996 | Kruger et al. | 128/204.26 |
| 5,787,882 | A | 8/1998 | Hamilton | |
| 6,394,091 | B1 | 5/2002 | Giorgini | |
| 7,673,630 | B2 * | 3/2010 | Kling | 128/207.12 |

FOREIGN PATENT DOCUMENTS

| | | | |
|---|---|---|---|
| DE | 695492 | A | 8/1940 |
| DE | 1153258 | B | 8/1963 |
| DE | 1945462 | U | 9/1966 |
| DE | 2720681 | B1 | 11/1978 |
| EP | 0011682 | A1 | 6/1980 |
| GB | 934213 | A | 8/1963 |
| GB | 1215218 | A | 12/1970 |

* cited by examiner

*Primary Examiner* — Patricia Bianco
*Assistant Examiner* — Nihir Patel
(74) *Attorney, Agent, or Firm* — The Webb Law Firm

(57) ABSTRACT

The invention relates to a respiratory protection mask for a compressed air breathing apparatus comprising a pulmonary machine which is controlled by a control membrane when the wearer of the mask breathes in. According to the invention, the air outlet of the expiratory valve and the control membrane are covered by a common cover, forming a rinsing area on the outside of the control membrane through which homogeneously temperate, clean rinsing air flows from the air outlet to the air discharge openings in the cover, thereby ensuring high functionality and high service life of the membrane-controlled pulmonary machine despite extreme environmental conditions.

4 Claims, 1 Drawing Sheet

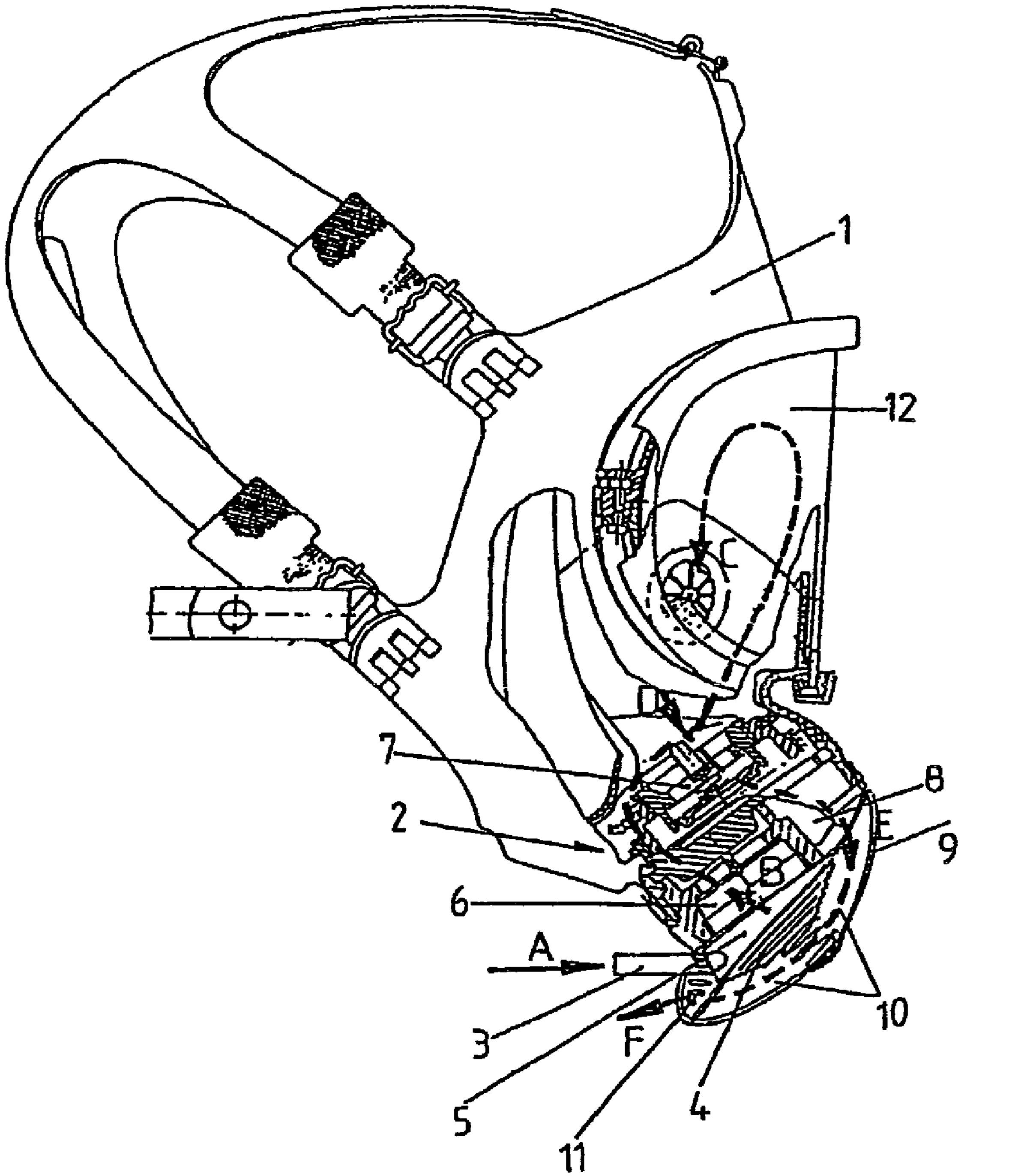
1
12
C
7
8
2
9
B
6
A
3
F
10
5
4
11

RESPIRATOR MASK FOR A COMPRESSED AIR BREATHING APPARATUS

CROSS REFERENCE TO RELATED APPLICATIONS

This application is a continuation of U.S. patent application Ser. No. 10/497,134, filed Oct. 18, 2004, now U.S. Pat. No. 7,673,630, which is a national stage filing under 35 U.S.C. 371 of PCT/DE02/03420, filed Sep. 10, 2002, which claims priority to German Application No. 101 59 219.1, filed Nov. 27, 2001, all of which are incorporated herein by reference in their entirety.

BACKGROUND OF THE INVENTION

1. Field of the Invention

This invention relates to a respirator mask for a compressed air breathing apparatus with a lung machine controlled by a control membrane and an expiratory valve with an air outlet.

2. Description of Related Art

Respirator masks, when combined with a compressed air respirator, are typically operated with a lung machine that is connected to the facepiece by a screwed or plug-in connection. The air supply from a pressure reducer via a medium-pressure line is controlled by a control membrane operated by the mask wearer's inhaling that mechanically acts on a control valve which in turn releases the medium-pressure line as required. The thin membrane made of an elastic material is of course highly sensitive to environmental conditions involving extreme temperatures and aggressive media. The functioning of the membrane may be impaired, for example, by reduced elasticity in low temperatures which adversely affects resistance to breathing and sensitivity, or if the membrane material is penetrated, destroyed, or severely mechanically damaged by aggressive gases such as hydrogen sulfide or phosgene.

SUMMARY OF THE INVENTION

It is therefore the problem of the invention to design a respirator mask of the type mentioned at the outset in such a way that the functioning of the control membrane is not impaired by temperatures and aggressive media and thus a long service life is ensured.

This problem is solved according to the invention by a respirator mask comprising the characteristics described in claim 1. The dependent claims disclose further advantageous improvements of the invention.

The general concept of the invention is a common lid that covers the air outlet of the expiratory valve and the control valve and that comprises air discharge openings on the opposite side, i.e., the side facing away from the air outlet. Thus a purging space or duct is created in which the mask wearer's clean expiratory air flows at a homogenous temperature from the air outlet across the surface of the control membrane and washes away the aggressive gases while keeping the membrane at an equal temperature, or cools or heats it depending on the outside temperature. This ensures undisturbed functionality and a long service life of the control membrane.

BRIEF DESCRIPTION OF THE DRAWING

An embodiment of the invention will be explained in greater detail below with reference to the only FIGURE showing a partial sectional view of a respiratory mask with a lung machine attached to it.

FIG. 1 is a partial sectional view of a respiratory mask with a lung machine attached to it, according to the present invention.

DESCRIPTION OF THE PREFERRED EMBODIMENTS

The facepiece 1 is equipped with a lung machine 2 for supplying respiratory air to the wearer of the mask from a compressed air reservoir via a pressure reducer and a medium-pressure line 3. Air supply is controlled according to the rhythm of breathing by an inhale-operated control membrane 4 that is connected via a linkage to a control valve (not shown) that opens the medium-pressure line 3 when the wearer inhales. Arrows A, B, and C show the path of the inhalation air along the dashed line from the medium-pressure line 3 via the chamber 5 and the air inlet 6 of the lung machine and along the visor panels 12 to the wearer of the mask while the used air is exhaled in the direction of arrows D, E, and F through the expiratory valve 7. As can be seen in the FIGURE, the air the wearer of the mask exhales does not immediately flow outside but through an air outlet 8 into the purging space 10 defined by the lid 9 above the control membrane 4. This means that clean and homogeneously tempered purging air, i.e. the exhalation air of the wearer of the mask, is conducted across the surface of the control membrane 4 with each exhalation cycle. This keeps the control membrane 4 at an equal temperature regardless of the outside temperature so that its functioning is neither limited by high nor by low outside temperatures. The control membrane 4 becomes neither too rigid nor too soft but keeps its predefined mechanical properties. Breathing conditions remain optimal for the wearer of the mask even under extreme conditions. Furthermore, aggressive toxic gases such as hydrogen sulfide or phosgene that can diffuse the thin control membrane relatively fast and harm the wearer of the equipment are continuously washed away from the control membrane 4 thereby eliminating the risk of impairment and ensuring a long service life and purity of the inhalation air. The exhaled air (purging air) is discharged through air discharge openings 11 in the lid 9.

LIST OF REFERENCE SYMBOLS

1 Facepiece
2 Lung machine
3 Medium-pressure line
4 Control membrane
5 Chamber
6 Air inlet
7 Expiratory valve
8 Air outlet
9 Lid
10 Purging space
11 Air discharge openings
12 Visor panels
Arrows A-B-C path of the inhaled air
Arrows D-E-F path of the exhaled air

The invention claimed is:

1. A respirator mask for compressed air breathing apparatuses comprising a lung machine controlled by a control membrane and an expiratory valve with an air outlet, wherein the air outlet of the expiratory valve and the control membrane of the lung machine are covered by a common lid spaced from the expiratory valve and the control membrane, the common lid comprising air discharge openings on the side of the lid that faces away from the air outlet and forming a purging space above the control membrane.

2. The respirator mask according to claim 1, wherein the lid for forming a duct is spaced a small distance from the control membrane to separate it the control membrane from the ambient atmosphere.

3. The respirator mask according to claim 2, wherein the lid is an integral part of the lung machine or the respirator mask or is separately attached to at least one of the lung machine or respirator mask.

4. The respirator mask according to claim 1, wherein the lid is an integral part of the lung machine or the respirator mask or is separately attached to at least one of the lung machine or respirator mask.

* * * * *

UNITED STATES PATENT AND TRADEMARK OFFICE

CERTIFICATE OF CORRECTION

PATENT NO. : 8,245,712 B2
APPLICATION NO. : 12/687522
DATED : August 21, 2012
INVENTOR(S) : Peter V. Kling It is certified that error appears in the above-identified patent and that said Letters Patent is hereby corrected as shown below:

Column 3, Line 5, Claim 2, after “separate” delete “it”

Signed and Sealed this
Thirteenth Day of November, 2012

David J. Kappos
*Director of the United States Patent and Trademark Office*